US009023810B2

(12) United States Patent
Piccirilli et al.

(10) Patent No.: US 9,023,810 B2
(45) Date of Patent: *May 5, 2015

(54) USE OF A COMPOUND COMPRISING D-MANNOHEPTULOSE AND/OR PERSEITOL FOR TREATING AND PREVENTING INNATE IMMUNITY MODIFICATION DISEASES

(75) Inventors: Antoine Piccirilli, Villennes sur Seine (FR); Nathalie Piccardi, Arceau (FR); Philippe Msika, Versailles (FR); François Paul, Montgauch (FR); Stéphanie Bredif, Chaudon (FR)

(73) Assignee: Laboratories Expanscience, Courbevoie (FR)

( * ) Notice: Subject to any disclaimer, the term of this patent is extended or adjusted under 35 U.S.C. 154(b) by 1037 days.

This patent is subject to a terminal disclaimer.

(21) Appl. No.: 12/929,684

(22) Filed: Feb. 8, 2011

(65) Prior Publication Data
US 2011/0274778 A1 Nov. 10, 2011

Related U.S. Application Data

(62) Division of application No. 11/587,961, filed as application No. PCT/FR2005/001075 on Apr. 29, 2005, now Pat. No. 7,897,579.

(30) Foreign Application Priority Data

Apr. 30, 2004 (FR) ..................................... 04 04635

(51) Int. Cl.
| | |
|---|---|
| *A61K 8/60* | (2006.01) |
| *A61Q 19/00* | (2006.01) |
| *A23L 1/30* | (2006.01) |
| *A61K 8/97* | (2006.01) |
| *A61K 31/7004* | (2006.01) |
| *A61K 36/48* | (2006.01) |

(52) U.S. Cl.
CPC ................ *A61K 8/60* (2013.01); *A61Q 19/007* (2013.01); *A23L 1/30* (2013.01); *A23L 1/3002* (2013.01); *A61K 8/97* (2013.01); *A61K 31/7004* (2013.01); *A61K 36/48* (2013.01); *A61K 2800/75* (2013.01); *A61Q 19/00* (2013.01); *A61Q 19/005* (2013.01); *A61Q 19/008* (2013.01)

(58) Field of Classification Search
CPC ... A61Q 19/007; A61Q 19/005; A61Q 19/00; A61K 8/60; A61K 8/97; A61K 31/7004; A61K 36/48
See application file for complete search history.

(56) References Cited

U.S. PATENT DOCUMENTS

| | | | |
|---|---|---|---|
| 4,722,843 A | 2/1988 | Vinson | |
| 6,146,616 A | 11/2000 | Msika et al. | |
| 6,861,077 B1 | 3/2005 | Cannell et al. | |
| 7,029,713 B2 | 4/2006 | Msika et al. | |
| 2002/0035071 A1* | 3/2002 | Pitha et al. | 514/23 |
| 2003/0092669 A1 | 5/2003 | Chapnick et al. | |
| 2003/0157050 A1 | 8/2003 | Ambrosen et al. | |
| 2004/0022882 A1 | 2/2004 | Piccirilli et al. | |
| 2004/0091493 A1 | 5/2004 | Perrier et al. | |
| 2004/0101580 A1 | 5/2004 | Msika et al. | |

FOREIGN PATENT DOCUMENTS

| | | |
|---|---|---|
| AU | 2003269064 | 2/2004 |
| FR | 2843125 A1 | 2/2004 |
| WO | WO 95/03809 A2 | 2/1995 |
| WO | WO 98/47479 A1 | 10/1998 |
| WO | WO 01/21150 A1 | 3/2001 |
| WO | WO 01/68040 A2 | 9/2001 |
| WO | WO 01/82889 A1 | 11/2001 |

OTHER PUBLICATIONS

"Face Masks" by Women Fitness [online] Retrieved from the internet on Jul. 9, 2014. Published on Apr. 4, 2004. Retreived from <http://www.womenfitness.net/beauty/skin/face_masks.htm>.*
Dreher, M.L., Davenport, A.J. (2013) Hass Avocado Composition and Potential Health Effects. Critical Reviews in Food Science and Nutrition, vol. 53, p. 738-750.*
Ikan, R. (1991) Natural Products: A Laboratory Guide, p. 79-81. Published by Academic Press.*
Adeyemi et al., "Analgesic and anti-inflammatory effects of the aqueous extract of leaves of *Persea americana* Mill (Lauraceae)," Fitoterapia, 2002, 73, 375-380.
Chediack et al., "Intestinal passive absorption of water-soluble compounds by sparrows: effect of molecular size and luminal nutrients," J. Comp. Physiol. B, 2003, 173, pp. 187-197.
Eslava et al., "Aqueous Extracts of Medicinal Plants, Interfere with Grow and Adherence to HEp-2 culture Cells of Bacterial Strains, Associated with Diarrhea Disease," Abstracts of the General Meeting of the American Society for Microbiology, 2001, vol. 101, p. 71, XP 009044130.
Gallagher et al., "The effects of traditional antidiabetic plants on in vitro glucose diffusion," Nutrition Research, 2003, 23, pp. 413-424.
Liu et al., "Human beta-defensin-2 production in keratinocytes is regulated by interleukin-1, bacteria, and the state of differentiation," J. Invest. Dermatol., Feb. 2002, 118(2), pp. 275-281, abstract only.
Raonimalala et al., "Effect of soluble carbohydrates from avocado fruit (*Persea gratissima* gaertner) on calcium utilization in rats," CAPLUS, 1980, XP 002986922, 1 pg.
Shaw et al., "High-Performance Liquid Chromatographic Analysis of D-*manno*-Heptulose, Perseitol, Glucose, and Fructose in Avocado Cultivars," J. Agric. Food Che.m, 1980, 28, pp. 379-382.
Macheleidt et al., "Deficiency of Epidermal Protein-Bound ω-Hydroxyceramides in Atopic Dermatitis," *The Journal of Investigative Dermatology*, vol. 119, No. 1, pp. 166-173, Jul. 2002.

(Continued)

*Primary Examiner* — Scarlett Goon
(74) *Attorney, Agent, or Firm* — Foley & Lardner LLP

(57) ABSTRACT

The invention relates to the use of a compound comprising D-mannoheptulose and/or perseitol for producing a drug for treating and/or preventing diseases related to the modification of an innate and/or acquired immunity by increasing the production of antimicrobial peptides, preferably hBD-2 without inducing inflammatory reactions, irritation or intolerance. Said compound can also comprise a peptidic avocado extract an/or a peptidic lupin extract.

7 Claims, No Drawings

(56) References Cited

OTHER PUBLICATIONS

Qiang et al., "Optimization of Physiological Lipid Mixtures for Barrier Repair," *The Journal of Investigative Dermatology*, vol. 106, No. 3, pp. 1096-1101, May 1996.

La Forge, "D-Mannoketoheptose, A new Sugar from the Avocado," *Preparation of d-mannoketoptose from the avocado*, pp. 511-522, 1916.

Merck Index, "D-manno-Heptulose," p. 806, 14$^{th}$ edition, 2006.

Human, "Oil as a byproduct of the avocado," *South African Avocado Growers' Association Yearbook*, vol. 10, pp. 159-162, 1987.

Duke, "Choosing Herbs That Heal," *The Green Pharmacy*, p. 394, 1997.

"Avocado Receives 'R' Rating," available online at http://www.living-foods.com/articles/avocado.html as of Jan. 2, 2002.

Bredif et al., "Avocado sugars are effective inducer of cutaneous defensive functions," *J. Am. Acad. Dermatol.*, pp. AB84, P1000, Feb. 2007.

Bajaj-Elliot et al., "Inate immunity in health and disease," *Molec. Immunol.*, vol. 42, No. 8, pp. 857-858, 2005.

De Heer et al., "Innate immunity as a driving force in renal disease," *Kidney International*, vol. 73, pp. 7-8, 2008.

Shaw et al., "High-Performance Liquid Chromatographic Analysis of D-manno-Heptulose, Perseitol, Glucose, and Fructose in Avocado Cultivars," *J. Agric. Food Chem.*, vol. 28, pp. 379-382, 1980.

Ong et al., "Engogenous Antrimicrobial Peptides and Skin Infections in Atopic Dermatitis," *N. Engl. J. Med.*, pp. 1151-1160, 2002.

Dorland's Medical Dictionary for Health Consumers, "Pharmaceutical," 2007.

Aroma Web, "Avocado Oil," www.webaroma.com, accessed Jun. 29, 2009.

Weiner et al., "Solid and Liquid Excipients," *Excipient Toxicity and Safety*, p. 186, 1999.

Notice of Allowance issued by the Examiner in U.S. Appl. No. 11/587,961 on Oct. 28, 2010.

Office Action issued by the Examiner in U.S. Appl. No. 11/587,961 on Mar. 15, 2010.

Office Action issued by the Examiner in U.S. Appl. No. 11/587,961 on Nov. 23, 2009.

Office Action issued by the Examiner in U.S. Appl. No. 11/587,961 on Jul. 9, 2009.

Office Action issued by the Examiner in U.S. Appl. No. 11/587,961 on Oct. 17, 2008.

Office Action issued by the Examiner in U.S. Appl. No. 11/587,961 on May 20, 2008.

Hagers Handbuch der Pharmazeutischen Praxis Drogen P-Z 5. Auflage, Springer Verlag Berlin Heidelberg, XP 002318088, 1994, pp. 69, 70, 72.

Haendler, "L'huile d'avocat et les produits derives du fruit," *Fruits*, vol. 20, No. 11, pp. 625-633, 1965.

\* cited by examiner

USE OF A COMPOUND COMPRISING D-MANNOHEPTULOSE AND/OR PERSEITOL FOR TREATING AND PREVENTING INNATE IMMUNITY MODIFICATION DISEASES

This application is a divisional of U.S. application Ser. No. 11/587,961, filed Oct. 27, 2006, which is a U.S. national stage application of PCT/FR2005/001075, filed Apr. 29, 2005, which claims priority to application FR 0404635 filed Apr. 30, 2004, all of which applications are incorporated herein by reference in their entirety.

The present invention relates to the use of a compound comprising D-mannoheptulose and/or perseitol for manufacturing a drug intended for treating and/or preventing diseases related to a modification of innate immunity.

All animal species are confronted on a daily basis with a large number of microorganisms, such as bacteria, fungi, parasites or viruses that can threaten their health or even their life. Two systems of defence oppose these microorganisms: a system called innate immunity that is common to all animals, including man, and a so-called adaptive or specific immunity system that is acquired thanks to cells and immunity mediators after contact with the potential aggressor.

The innate or adaptive immunity responses differ in their recognition mechanisms for these microorganisms. In innate immunity, the specificity of the receptors is genetically determined from birth and does not change. These receptors are expressed on the cells such as certain epithelial and endothelial cells, dendritic cells, monocytes and macrophages. All the structures recognised by the innate immunity receptors are common to a very great number of microorganisms. In contrast to the adaptive immunity response, the innate immunity response mechanisms (phagocytosis, antimicrobial peptides, etc.) are activated at the onset of the infection and control almost immediately the proliferation of pathogens that invade the host. The adaptive immunity response then takes over.

Anti-microbial peptides have been found in both the vegetal and animal kingdoms, and more than 500 anti-microbial peptides have been discovered from insects to man. The anti-microbial peptides are small molecules (10 to 50 amino acids) capable of destroying a wide variety of microorganisms (Gram+ and/or Gram−, fungi, viruses, transformed cells), by rendering their cellular membrane permeable. Moreover, certain of these antimicrobial peptides, through their chemo-attractive properties, are able to recruit the cells participating in the adaptive immunity, such as the dendritic cells or still more the lymphocytes T. Numerous antimicrobial peptides have been found in the vernix caseosa and in the amniotic fluid, as well as in the skin of the newborn, suggesting their key role in the antimicrobial defence during birth, but also from the beginning of the life while the acquired immunity is still immature.

Most organisms synthesise several types of antimicrobial peptides at the level of their different epithelia in order to define a wide spectrum of activity. In the mammals, two major classes of antimicrobial peptides, whose production is induced by contact with a microorganism, have been described: the cathelicidins and the defensins.

Human cathelicidin (LL-37) was isolated for the first time from bone marrow cells. LL-37 is principally expressed in the human skin, in the nails, as well as in the healthy and inflamed synovial membrane, notably in patients afflicted with arthritis. LL-37 has a wide spectrum of activity and seems to act in synergy with other antimicrobial peptides, notably the defensins. LL-37 also has chemo-attractant properties, which enable it to recruit adaptive immunity cells.

On the basis of their secondary structure, the defensins are themselves divided into two families, α et β. The α-defensins (6 known at present) are located mainly in the storage granules of specialised cells such as the neutrophiles, or the Paneth intestinal cells, whereas the β-defensins are characteristics of the epithelial tissues. Apart from their role in innate immunity, the defensins are equally known for their mitogenic properties, which suggest their potential implication in healing processes.

In man, 4 β-defensins have been identified up to now (more than 20 genes that encode for antimicrobial peptides are believed to exist in our genome). The human β-defensin 1 (hBD-1) is generally produced constitutively and is expressed in major quantities in the liver and to a lesser extent in the pancreas, the saliva glands, the epithelia of the respiratory system, in the female uro-genital system, in the healthy synovial membrane, as well as in the placenta. hBD-1 is also expressed in the skin. The other forms of β-defensins, hBD-2, 3 and 4, are inducible. hBD-3 is induced in the inflammatory synovial membranes such as for example in arthritic pathologies. The expression of hBD-2 has so far been reported in the skin, the uro-genital tract, the sudoral glands and in the pilosebacic unit.

In the skin, other peptides or proteins, such as adrenomedulin, cystatin, the specific inhibitor for elastase/SKALP/elafin, are supposed to possess antimicrobial activities. More recently, dermicidin (broad spectrum of activity) has been characterised as a specific antimicrobial peptide for the skin, which is supposedly produced in the eccrinal sudoral glands, and whose simultaneous secretion with sweat supposedly constitutes an important part of the innate defence system against local and systemic infections. For the first time, hBD-2 has been characterised in psoriasis squames. The expression of hBD-2 and 3, as well as LL-37, is increased in psoriasis lesions, thus explaining the greater resistance to infections of patients who are afflicted by this pathology. On the other hand, in atopic dermatitis (chronic lesions and erupting lesions), the expression of LL-37 and hBD-2 is diminished under the influence of interleukine-4 (IL-4) and interleukine-13 (IL-13), mediators of atopy. This deficiency could explain the increased susceptibility to infections of patients suffering from atopic dermatitis. For acne, the expression of the β-defensins (hBD-1 and 2) is increased as a reaction against the proliferation of *P acnes*. Moreover, it is supposed that people with acne suffer from an initial imbalance in antimicrobial peptides responsible for the bacterial proliferation, bacteria that in return stimulate the innate immunity defences.

Inflammation therefore seems to be a preponderant factor in the induction of antimicrobial peptides. In addition, it has also been shown that interleukine-1, the TNF-α (Tumor Necrosis alpha), and ultra violet irradiation stimulate the production of hBD-2. The expression of hBD-2 is also linked to the differentiation state of the keratinocytes. Thus, the stimulation of the production of antimicrobial peptides, notably from the family of the defensins, and more particularly hBD-2, would permit the promotion and/or the re-establishment of the innate immunity, notably of the eyes and the epithelia (epidermis, vaginal, intestinal, nasal and auricular mucosa, respiratory passages).

The buccal cavity is constantly exposed to a great variety of microbes (bacteria, viruses, fungi). It is well established that bacteria, inter alia, such as actinobacillus actinomycetemcomitans, porphyromonas gingivalis, are the key factors that participate in the development of parontal diseases (gingivitis and parodontitis). The gingival epithilium constitutes the first wall of defence against different pathogens present in the buccal environment. In this regard, the gingival keratinocytes produce a broad panel of antimicrobial peptides, hBD-1, -2, 3, LL37. These peptides are also produced in the buccal mucous membrane and by the salivary glands.

More particularly, the stimulation of the antimicrobial peptides would permit the innate immunity to be boosted and/or re-established in the healthy or pathological skin of babies and children, whose immunity is generally deficient, and in adults' or healthy or sick old peoples' skin (immuno-depressives). This stimulation would therefore advantageously complete the passive defence system of the skin, which is constituted by the stratum corneum (corneocytes+intercellular cement), and prepare the adaptive immunity response in babies, children, adults and the elderly, be they in good health or sick. At the same time, cicatrisation would also be promoted.

D-mannoheptulose, the first ketoheptose to be identified in 1916 by La Forge, has the general formula (I)

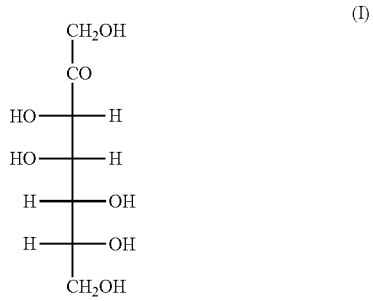

and is found in certain plants, especially in lucerne or alfalfa *Medicago sativa* L.), avocado, figs (*Ficus officinalis* L.) and the primrose (*Primula officinalis* Jacq.). However, the highest contents of D-mannoheptulose are to be found in the avocado. D-mannoheptulose has already been used in therapeutic applications. For example, the patent application WO95/03809 describes the use of D-mannoheptulose as a glucokinase inhibitor for the inhibition of the development of tumorous cells, and the application US2003/0092669 describes an oral nutritional supplement comprising D-mannoheptulose, which can lower the level of insulin and thereby enables a loss in weight.

Perseitol, the polyol form of D-mannoheptulose, has the general formula (II)

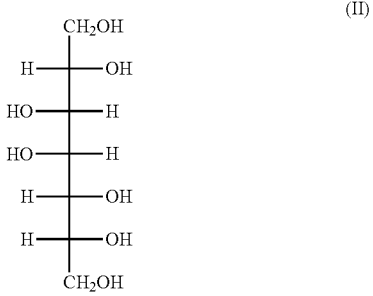

and is also found in the avocado, in particular in the fruit or in the avocado stone.

According to the publication "Search for pharmacochemical leads from tropical rainforest plants", Hitotaka Shibuya et al. Pure Appl. Chem., vol. 71, n° 6, pp 1109-1113, 1999, perseitol, associated with a potassium ion, enables leucine-3H to be incorporated into tumorous cells of Ehrlich ascites sarcoma.

Surprisingly, the inventors have found that a composition comprising D-mannoheptulose and/or perseitol enables an increase in the production of antimicrobial peptides, advantageously hBD-2, without inducing inflammatory reactions, irritations or intolerance, notably without significantly stimulating the secretion of molecules that are usually expressed in the case of inflammatory reactions.

Accordingly, the object of the present invention is the use of a compound comprising D-mannoheptulose and/or perseitol and an appropriate pharmaceutically acceptable excipient for the manufacture of a drug or a veterinary composition intended for treating and/or preventing diseases related to a modification of innate immunity and/or acquired by an increased production of antimicrobial peptides, of the family of the cathelicidins and/or of the beta-defensins, advantageously of hBD-2. In the scope of the present invention, the term "modification" can mean increase or decrease.

The present invention also relates to the use of a composition comprising D-mannoheptulose and/or perseitol and an appropriate pharmaceutically acceptable excipient for the manufacture of a drug or a veterinary composition intended for treating and/or preventing diseases related to a modification of innate immunity and/or acquired by an increased production of antimicrobial peptides, such as a specific inhibitor of elastase, particularly the elafin (SKALP).

The drug or the veterinary composition according to the invention advantageously permits the innate immunity and/or the acquired immunity to be stimulated and/or completed.

Generally, in the context of the present invention, said diseases can be linked to the presence of microorganisms, notably the Gram+ and/or Gram− bacteria, fungi, yeasts or viruses.

More particularly, said diseases can be some infections of the ocular and auditory systems, of the non-keratinised epithelia (vaginal, intestinal, gingival, pulmonary, respiratory tract, anal and urethral mucosa) and of the keratinised epithelia such as the skin. Said diseases can also be some infections of the phanera or cuteaneous appendages (hair, nails, sudoral glands, sebaceous glands). Consequently, said diseases can be pathologies such as folliculitis, boils, abscesses, impetigo or panaris.

Said diseases can be pathologies of the scalp such as dandruff and more widely the affections related to a hyper-seborrhoea.

Said diseases can be pathologies associated with a modification of the Th1/Th2 balance such as atopic dermatitis.

Said diseases can be pathologies associated with a modification of the cytokine synthesis, such as the IL-4 and/or the IL-13, notably in the context of atopic dermatitis.

Said diseases can also be the inflammatory dermatoses, such as atopic dermatitis, atopic and/or contact eczema, psoriasis, acne and irritations of the skin.

Said diseases can also be burns, in particular the first degree and second degree burns.

Said diseases can also be pathologies associated with a deficit of the cuteaneous barrier. Accordingly, the drug according to the invention can be used for the treatment of skin that is hyper-reactive, (sensitive, irritated, allergic), atopic, dry or aged. Said diseases can also be pathologies associated with skin, rendered fragile by an environmental aggression, notably caused by the cold, pollution, stress, tobacco, sun exposure.

In the context of the present invention, the drug is also suitable for protecting immature, healthy or pathological skin of babies and children. In fact, it enables the natural defences of the epidermis of the child to be reinforced, whose immunity is generally deficient.

In the context of the present invention, the drug is also suitable for protecting healthy or pathological skin of adults or of the elderly, notably of immuno-depressive individuals.

The drug according to the invention is also suitable for encouraging cicatrisation in the process of normal or pathological cicatrisation, such as ulcers and scabs.

In the context of the present invention, the drug is also aimed at the treatment and/or prevention of parodontal diseases, inflammatory articular pathologies such as arthritis, of mucous infections, notably of the vaginal, intestinal, respiratory, nasal or auricular mucosa, or infections of the ocular system.

The composition according to the invention advantageously comprises 0.001 to 30% dry weight of D-mannoheptulose, based on the total weight of the composition, even more advantageously 0.01-20% dry weight, even more advantageously 0.01-10% dry weight, even more advantageously 0.5-5% dry weight of D-mannoheptulose. The composition according to the invention advantageously comprises 0.001 to 30% dry weight of perseitol, based on the total weight of the composition, even more advantageously 0.01-20% dry weight, even more advantageously 0.01-10% dry weight, even more advantageously 0.5-5%% dry weight of perseitol. In the context of the present invention, the terms "D-mannoheptulose" and "perseitol" also include their chemical derivatives.

The source of D-mannoheptulose and/or perseitol can be a hydrosoluble extract of sugars from avocado or another plant. Otherwise, D-mannoheptulose and perseitol are commercially available (synthetic origin). According to an advantageous variant of the invention, the source of D-mannoheptulose and/or perseitol is a hydrosoluble extract of sugars from avocado.

The hydrosoluble extract of sugars from avocado can be directly obtained from any part of the avocado or the avocado tree, such as the fruit, the skin, the stone, the leaf or the roots of the avocado tree. It is also possible to obtain a peptidic extract from the co-products from the avocado conversion industry, among which can be cited in a non-limiting way: fresh avocado pulp, frozen pulp, dehydrated pulp, avocado oil cake obtained from oil extraction processes (mechanical and/or solvent extraction of previously dehydrated fruit), de-oiled solids resulting from wet oil-extraction processes (centrifugation processes), de-oiled solids resulting from enzymatic extraction processes of avocado, raw avocado mash (guacamole), solid waste resulting from production units of these mashes. The extract is advantageously obtained from fresh fruit of the avocado tree. The fruits may be chosen from among the varieties Hass, Fuerte, Ettinger, Bacon, Nabal, Anaheim, Lula, Reed, Zutano, Queen, Criola Selva, Mexicana Canta, Region Dschang, Hall, Booth, Peterson, Collinson Redn, more advantageously among the varieties Hass, Fuerte and Reed. The varieties Hass, Fuerte, Ettinger and Bacon are preferred, and more advantageously the varieties Hass and Fuerte.

The avocado fruit is principally constituted by water, the pulp, the oil and the stone. The proportions of these constituents are, as is the case for all natural and vegetal products, extremely variable. Nevertheless, it is generally agreed that the figures given in Table 1, expressed in percent of fresh fruit, reflect the average compositions:

TABLE 1

| | |
|---|---|
| Water | 70-85% |
| Proteins | 1.5-4.5% |
| Lipids | 12-23% |
| Sugars | 1.5-5% |
| Fibres | 1.1-1.6% |

In fact, the avocado is not particularly rich in polysaccharides. However, the nature of the soluble monosaccharides is very special, such as the perseitol or the D-mannoheptulose constituted by 7 carbon atoms.

The hydrosoluble extract of sugars from the avocado may be obtained by a process comprising the following successive steps:
  obtaining an avocado oil cake, advantageously from the avocado fruit, by drying the avocado then extracting the lipids (oil); then
  cryogenic grinding and total delipidation of said oil cake, then decanting and centrifuging so as to recover the soluble fraction rich in C7 sugars (elimination of the cake);
  demineralisation over an ionic resin of said soluble fraction obtained from the preceding step; then
  ultrafiltration at 10000 daltons; and
  optionally, concentration under vacuum and packaging.

The first step of the process consists in drying the fruit and then extracting the oil. After slicing the fruit into thin slices, it can be dried by any of the techniques known to the person skilled in the art, among which may be cited hot air drying, lyophilisation or even osmotic drying. In general, the temperature is advantageously maintained during this drying step at below or equal to 80° C., whatever the technique employed. In the context of the present process, for reasons of ease of application and for cost reasons, drying in ventilated dryers, in thin films and under a current of hot air is preferred at a temperature comprised between and 75° C. The operation can vary between 5 and 72 hours.

The lipids from the dried fruit are then extracted either mechanically in a continuous screw press, or chemically, with a solvent such as hexane, in a soxhelet extractor or in a continuous band extractor of the de Smet® type, notably according to the process described in the application FR 2 843 027, or by a process using supercritical $CO_2$. Among the major interests of the process, the oil co-product constitutes a product that obviously has a commercial value. This is the reason why a mechanical extraction of the lipids is preferred. The dry and de-oiled fruit, also called oil cake, can be subjected to the following steps:
  cryogenic grinding
  total delipidation, especially with acetone and/or ethanol, decanting then washing the oil cake with water,
  centrifuging, recovery of the soluble fraction (elimination of the cake),
  demineralisation by ion-exchange
  ultrafiltration with a size threshold of 10 kD
  concentration under vacuum, addition of preservatives and packaging.

In general, the final aqueous extract can comprise 0.1 to 10 wt. % of dry matter, advantageously 1 to 7 wt. % of dry matter, even more advantageously 3 to 5 wt. % of dry matter. The C7 sugar content, i.e. D-mannoheptulose and perseitol in the dry matter advantageously comprises to 90 wt. %, based on the total weight of the dry matter. Average analytical data for an aqueous solution comprising 5% dry extract, obtained by the previously described process, are given in the Table 2:

TABLE 2

| | | |
|---|---|---|
| pH (dilution ¼) | | 4.5-7.5 |
| Absorbance (dilution ½) | 420 nm | less than 0.2 |
| | 550 nm | less than 0.05 |
| C7 sugars/dry matter | | 65-90% |

The relative concentration of sugars in the hydrosoluble extract, in weight based on the total weight of the dry matter in the extract conforms advantageously to the following criteria (relative composition determined by HPLC, high performance liquid chromatography):

| | |
|---|---|
| D-mannoheptulose | 5 to 80% |
| Perseitol | 5 to 80% |
| Saccharose | less than 10% |
| Glucose | less than 10% |
| Fructose | less than 10% |

The hydrosoluble extract of avocado sugars advantageously comprises, based on the total weight of dry matter, 10 to 80 wt. % of D-mannoheptulose, more advantageously 15 to 70 wt. % of D-mannoheptulose. The hydrosoluble extract of avocado sugars advantageously comprises, based on the total weight of dry matter, 20 to 80 wt. % of perseitol, more advantageously 25 to 70% wt. % of perseitol.

Preferably, the relative composition of sugars in the hydrosoluble extract, in weight based on the total weight of the dry matter in the extract conforms to the following criteria (relative composition determined by HPLC):
  D-mannoheptulose 25 to 60%
  Perseitol 25 to 60%
  Saccharose less than 10%
  Glucose less than 10%
  Fructose less than 10%

Surprisingly, the inventors have observed a synergistic effect between the D-mannoheptulose and/or perseitol and the minor sugars (fructose, glucose, saccharose) present in the extract of the avocado sugars.

Optionally, the obtained extract can be lyophilised to obtain a completely soluble, solid powder (dry extract).

According to an advantageous variation of the invention, the composition further comprises a peptidic extract of avocado, advantageously in a proportion of 0.001 to 30% dry weight, even more advantageously 0.01 to 20% dry weight, even more advantageously 0.1 to 15% dry weight, even more advantageously 0.5 to 10% dry weight, even more advantageously 0.7 to 8% dry weight and even more advantageously 1 to 5% dry weight, based on the total weight of the composition. Then, a synergistic effect is advantageously observed.

The peptidic extract of avocado, added in the composition according to the invention, advantageously comprises 2 to 10 wt. % of alpha-amine nitrogen, based on the weight of the dry matter of the peptidic extract. In the context of the present invention, the terms "alpha-amine nitrogen" is understood to mean the content of nitrogen of the peptides in the form of free alpha-amine groups. The content of alpha-amine nitrogen in the peptides allows the degree of hydrolysis of the proteins, as well as the average molecular weight of the peptides to be estimated.

More particularly, the peptidic extract of avocado may be obtained by a process comprising the following steps:
  obtaining an avocado oil cake, advantageously from the avocado fruit, by drying the avocado then extracting the lipids; then cryogenic grinding and total delipidation of said oil cake, then decanting, centrifuging and recovery of the cake; then
  first hydrolysis in the presence of glucanases, followed by a centrifugation and the elimination of the soluble fraction;
  second hydrolysis in the presence of one or a plurality of proteases, followed by a centrifugation and the elimination of the deposit; then
  concentrating the peptidic phase by nanofiltration;
  discoloration, in the presence of active carbon, for example, followed by a simple filtration (10 µm) then an ultrafiltration (cut-off threshold of 10 kD); finally
  optionally, a final sterilizing microfiltration (0.2 µm), addition of preservative and packaging.

The method to obtain the oil cake of avocado and the extraction of the lipids are advantageously carried out in the same manner for the peptidic extract of avocado and the sugars of avocado. The dry and de-oiled fruit, also called oil cake, can then be subjected to the following steps:
  cryogenic grinding
  total delipidation, especially with acetone and/or ethanol,
  decanting then washing the oil cake with water,
  centrifugation, recovery of the cake,
  first hydrolysis in the presence of one or a plurality of glucanases,
  centrifugation, elimination of the soluble fraction,
  second hydrolysis in the presence of one or a plurality of proteases,
  centrifugation, elimination of the residue,
  concentration by nanofiltration
  discoloration, notably in the presence of active carbon,
  simple filtration (10 µm) then ultrafiltration (cut-off threshold 10 kD),
  filling and addition of preservative,
  final sterilizing microfiltration (0.2 µm)
  addition of preservative and packaging.

The final aqueous extract can comprise 1 to 60 wt. % of dry matter, or even 3 to 20 wt. % of dry matter, preferably 5 to 6 wt. % of dry matter. Optionally, the obtained extract can be lyophilised to obtain a solid powder (dry extract), but completely hydrosoluble with regard to the original proteins of the avocado. Based on the weight of the dry matter, the alpha-amine nitrogen content can be comprised between 2 and 10 wt. %, preferably between 5 and 7 wt. %. The pH of an aqueous solution with 1.2 wt. % of dry extract, based on the weight of the dry matter, will be generally comprised between 3 and 6, more advantageously between 4 and 5.

According to an advantageous variation of the invention, the composition further comprises a peptidic extract of lupine, advantageously in a quantity by weight of 0.001 to 30% of dry matter, even more advantageously of 0.01 to 10% of dry matter, based on the total weight of the composition. The peptidic extract of lupine, added in the composition according to the invention, comprises at least 70%, advantageously at least 80 wt. % of peptides, based on the weight of the dry matter of the peptidic extract. Then, a synergistic effect is advantageously observed.

In particular, the peptidic extract of lupine may be obtained by a process comprising the following steps:
  preparation of an oil cake of ground lupine or of a micronised flour of lupine;
  then, delipidation by solvent extraction
  extraction of soluble protein and -osidic fractions, or precipitation of the proteins at the isoelectric point;
  if need be separation of the protein fraction;
  enzymatic hydrolysis of the protein fraction and recovery, after an optional filtration, of the peptidic extract.

The process for preparing a peptidic extract is described in the French patent application FR 2 792 202, filed by Expanscience laboratories.

In addition, the composition can comprise at least one compound selected from the group constituted by the emollients, hydrating agents, activators of the keratin synthesis, keratoregulators, keratolytics, restructuring agents for the cuteaneous barrier (activators of the synthesis of cuteaneous lipids, PPAR agonists or Peroxysome Proliferator Activated Receptor), activators in the differenciation of keratinocytes (retinoids, Calcidone®, calcium), antibiotics, antibacterials agents, fungicides, anti-virals, sebo-regulators, such as the inhibitors of 5-alpha reductase, especially the active 5-alpha Avocuta® commercialised by les Laboratoires Expanscience, immunomodulators, such as tacrolimus, pimecrolimus, oxazolines, preservatives, anti-itching agents, the soothing agents, sun filters and sun screens, antioxidants, growth factors, healing agents or eutrophic molecules, the drugs and anti-inflammatory agents, and the compounds comprising vegetal oil insaponifiables.

In the context of the present invention, the activators for the synthesis of keratin, which can be used in association with D-mannoheptulose and/or perseitol are advantageously retinoids, peptides of lupine (commercialised by the Silab company), key proteins of stratum corneum or granulosum (keratins).

In the context of the present invention, antibiotics that can be used in association with D-mannoheptulose and/or perseitol are advantageously fucidic acid, penicillin, tetracyclines, pristinamycine, erythromycine, clindamycine, mupirocine, minocycline, doxycycline. In the context of the present invention; anti-viral agents that can be used in association with D-mannoheptulose and/or perseitol are advantageously Pacyclovir and valacyclovir. In the context of the present invention, anti-itching agents that can be used in association with D-mannoheptulose and/or perseitol are advantageously glycine, sugars and/or peptides of lupine, Cycloceramide® (oxazoline derivative).

In the context of the present invention, soothing agents that can be used in association with D-mannoheptulose and/or perseitol are advantageously alpha bisabolol, the derivatives of liquorice. In the context of the present invention, keratoregulators that can be used in association with D-mannoheptulose and/or perseitol are advantageously alpha hydroxyacids and their derivatives. In the context of the present invention, a keratolytic that can be used in association with D-mannoheptulose and/or perseitol is especially salicylic acid and its derivatives. In the context of the present invention, antioxidants that can be used in association with D-mannoheptulose and/or perseitol are advantageously vitamins (C, E), trace elements (copper, zinc, selenium). In the context of the present invention, growth factors that can be used in association with D-mannoheptulose and/or perseitol are advantageously becaplermine and TGF-beta (Transforming Growth Factor beta).

In the context of the present invention, healing agents that can be used in association with D-mannoheptulose and/or perseitol are advantageously vitamin A, panthenol, Avocadofurane®, zinc oxide, magnesium oxide, silicon oxide, madecassic or asiatic acid.

In the context of the present invention, drugs that can be used in association with D-mannoheptulose and/or perseitol are advantageously drugs that are suitable for topical or oral administration, for the prevention and/or treatment of atopis (corticoids, emollients), of acne (antibiotics, benzoyl peroxide, retinoids, azelaic acid, vitamin PP, zinc, cyclines), of eczema (immunomodulators, emollients, salmon oil, borage oil, prebiotics) of psoriasis (corticoids, calcipotriol, calcitriol, tazarotene, cade oil, acitretine, PUVA therapy). In the context of the present invention, anti-inflammatory agents that can be used in association with D-mannoheptulose and/or perseitol are advantageously steroidal anti-inflammatory agents (AIS), such as corticoids, or non-steroidal anti-inflammatory agents.

In the context of the present invention, restructuring agents of the cuteaneous barrier that enable the stimulation of the synthesis of the key lipids of the epidermis and which can be used with a synergistic effect in association with D-mannoheptulose and/or perseitol are advantageously linoleic concentrates of sunflower, such as the agent commercialised by the Laboratoires Expanscience, Soline® (see the international patent application WO 01/21 150), insaponifiables of vegetal oils, such as Avocadofurane® (see the international patent application WO 01/21 150), agonists PPAR (rosiglitazone, pioglitazone). The restructuring agents are advantageously present in a proportion of 0.001 to 30 wt. %, based on the total weight of the composition or the drug. In the context of the present invention, anti-fungals that can be used in association with D-mannoheptulose and/or perseitol are advantageously econazole and ketoconazole.

In the context of the present invention, antiseptic preservatives that can be used in association with D-mannoheptulose and/or perseitol are e.g. triclosan, chlorhexidine, the quaternary ammoniums. In the context of the present invention, immunomodulators that can be used in association, advantageously with a synergistic effect with D-mannoheptulose and/or perseitol are advantageously tacrolimus, pimecrolimus and the oxazolines.

In the context of the present invention, oxazolines that can be used in association, advantageously with a synergistic effect with D-mannoheptulose and/or perseitol are advantageously the oxazolines selected from the group consisting of 2-undecyl-4-hydroxymethyl-4-methyl-1,3-oxazoline, 2-undecyl-4,4-dimethyl-1,3-oxazoline, (E)-4,4-dimethyl-2-heptadec-8-enyl-1,3-oxazoline, 4-hydroxymethyl-4-methyl-2-heptadecyl-1,3-oxazoline, (E)-4-hydroxymethyl-4-methyl-2-heptadec-8-enyl-1,3-oxazoline, 2-undecyl-4-ethyl-4-hydroxymethyl-1,3-oxazoline. Even more advantageously, said oxazoline is 2-undecyl-4,4-dimethyl-1,3-oxazoline, called OX-100 or Cycloceramide®.

In the context of the present invention, compounds comprising insaponifiables of vegetal oils that can be used, advantageously with a synergistic effect, in association with D-mannoheptulose and/or perseitol are advantageously selected from the group constituted by the furanic lipids of the avocado, insaponifiables of the avocado and of soya, concentrates of lupine oil, concentrates of sunflower oil and their mixtures.

In the context of the present invention, the furanic lipids of the avocado that can be used, advantageously with a synergistic effect, in association with D-mannoheptulose and/or perseitol are advantageously the natural 2-alkyl furans, especially Avocadofurane®, commercialised by the Laboratoires Expanscience, which can be obtained by the process described in the international patent application WO 01/21605.

In the context of the present invention, the insaponifiables of avocado and soya that can be used, advantageously with a synergistic effect, in association with D-mannoheptulose and/or perseitol are advantageously a mixture of furanic insaponifiables of avocado and the insaponifiables of soya, in a ratio of about 1/3-2/3. The insaponifiables of avocado and soya are even more advantageously the product Piascledine®, commercialised by the Laboratoires Expanscience.

In the context of the present invention, the concentrates of lupine oil that can be used in association, advantageously with a synergistic effect with D-mannoheptulose and/or perseitol are advantageously the concentrates obtained by molecular distillation of lupine oil, advantageously sweet white lupine oil, such as those described in the international patent application WO 98/47479. Advantageously, they comprise about 60 wt. % of insaponifiables.

In the context of the present invention, the concentrates of sunflower oil that can be used in association, advantageously with a synergistic effect with D-mannoheptulose and/or perseitol are advantageously the linoleic concentrates of sunflower oil, such as the active principle commercialised by the Laboratoires Expanscience, Soline® (see the international patent application WO 01/21150).

The composition according to the invention can be formulated in the form of different preparations adapted for a topical administration, oral, rectal, vaginal, nasal, auricular or bronchial administration, to a parenteral administration. Preferably, these different preparations are adapted for a topical administration and include creams, ointments, lotions, oils, patches, sprays or all other products for external application. The administration modes, the posologies and the optimal galenical forms of the compounds and compositions according to the invention can be determined according to the criteria that are generally considered for establishing, in particular, a dermatological or veterinarial pharmaceutical treatment adapted to a patient or an animal, such as, for example the age and body weight of the patient or animal, the gravity of the general state, the tolerance to the treatment, the secondary effects and the skin type. Depending on the desired type of administration, the composition and/or the active compounds in accordance with the invention can also comprise at least one pharmaceutically, particularly dermatologically acceptable excipient. Preferably, an excipient adapted for an external topical administration is used. The composition according to the present invention can further comprise at least one pharmaceutical adjuvant known to the person skilled in the art and selected among the thickeners, the preservatives, the perfumes, the colorants, the mineral or chemical filters, the moisturisers, the spa waters, etc.

The present invention also relates to a drug or a veterinary composition comprising 0.001 to 30 wt. % of D-mannoheptulose and 0.001 to 30 wt. % of perseitol, based on the total weight of the drug, even more advantageously 0.01 to 10 wt. % of D-mannoheptulose and 0.01 to 10 wt. % of perseitol, and a pharmaceutically appropriate excipient.

The drug or the veterinary composition according to the invention can be formulated in the form of different preparations adapted for a topical administration, for an oral, rectal, vaginal, nasal, auricular or bronchial administration, for a parenteral administration. The administration modes, the posologies and the optimal galenical forms of the drug or the veterinary composition according to the invention can be determined according to the criteria that are generally considered for establishing, in particular, a dermatological pharmaceutical treatment adapted to a patient or a veterinarial treatment.

The present invention also relates to a cosmetic composition comprising 0.001 to 30 wt. % of perseitol and 0.001 to 30 wt. % of D-mannoheptulose, based on the total weight of said composition, even more advantageously 0.01 to 10 wt. % of perseitol and 0.01 to 10 wt. % of D-mannoheptulose. According to an advantageous variant of the invention, the source of D-mannoheptulose and/or perseitol is a hydrosoluble extract of sugars from avocado, which can be obtained according to a process such as that described above. Indeed, there exists a synergistic effect between the D-mannoheptulose, the perseitol and the minority sugars (fructose, glucose, saccharose) of the avocado.

According to an advantageous variant of the invention, the composition further comprises a peptidic extract of avocado, advantageously in a synergistic amount. The peptidic extract of avocado is advantageously present in a quantity of 0.001 to 30%, more advantageously 0.01 to 10%, dry weight, based on the total weight of the composition. The peptidic extract of avocado, added in the composition according to the invention, advantageously comprises 2 to 10 wt. % of alpha-amine nitrogen, based on the weight of the dry matter of the peptidic extract. It can be obtained according to a process such as that described above.

According to an advantageous variant of the invention, the composition further comprises a peptidic extract of lupine, advantageously in a synergistic amount. The peptidic extract of lupine is advantageously present in a quantity of 0.001 to 30%, more advantageously 0.1 to 10%, dry weight, based on the total weight of the composition. The peptidic extract of lupine, added in the composition according to the invention, comprises at least 70%, advantageously at least 80 wt. % of peptides, based on the weight of the dry matter of the peptidic extract. It can be obtained according to a process such as that described above.

In addition, the composition can comprise at least one compound selected from the group constituted by the restructurants of the cuteaneous barrier and the compounds comprising the insaponifiables of vegetal oils, such as described previously, advantageously in a synergistic amount. In particular, the cosmetic composition can comprise an active principle selected from the group consisting of Soline®, Avocadofurane® and Piascledine®, commercialised by the Laboratoires Expanscience. The composition according to the invention advantageously comprises 0.001 to 30 wt. %, based on the total weight of the composition, of at least one restructurant of the cuteaneous barrier.

The cosmetic composition according to the invention can be formulated in the form of different preparations adapted for a topical administration, an oral or rectal, vaginal, urethral, auricular, nasal or bronchial administration. Preferably, these different preparations are adapted for a topical administration and include creams, ointments, lotions, oils, patches, sprays or all other products for external application. Depending on the desired type of administration, the composition and/or the active compounds in accordance with the invention can also comprise at least one cosmetically acceptable excipient. The cosmetic composition according to the present invention can further comprise at least one cosmetic adjuvant known to the person skilled in the art and selected among the thickeners, the preservatives, the perfumes, the colorants, the mineral or chemical filters, the moisturisers, the spa waters, etc.

The present invention also relates to a cosmetic method of treatment of sensitive, irritated, allergic, dry, aged, intolerant skin and/or the mucosa presenting a disorder of the cuteaneous barrier, rendered fragile by an environmental aggression and exhibiting cuteaneous redness, or exhibiting an immunological, non pathological disequilibrium, characterised in that it consists of applying a composition according to the invention on the skin and/or the mucosa.

Finally, the present invention relates to a nutraceutical composition comprising D-mannoheptulose and/or perseitol and an acceptable excipient appropriate for food. The nutraceutical composition according to the invention advantageously comprises 0.001 to 30% wt. % of D-mannoheptulose, based on the total weight of said composition, even more advantageously 0.01 to 10 wt. % of D-mannoheptulose. The nutraceutical composition according to the invention advantageously comprises 0.001 to 30 wt. % of perseitol, based on the total weight of said composition, even more advantageously 0.01 to 10 wt. % of perseitol. The nutraceutical composition according to the invention advantageously comprises 0.001 to 30 wt. % of perseitol and 0.001 to 30 wt. % of D-mannoheptulose, based on the total weight of said composition, even more advantageously 0.01 to 10 wt. % of perseitol and 0.01 to 10 wt. % of D-mannoheptulose. According to an advantageous variant of the invention, the source of D-mannoheptulose and/or perseitol is a hydrosoluble extract of sugars from avocado, which can be obtained according to a process such as that described above.

According to an advantageous variation of the invention, the composition further comprises a peptidic extract of avocado, advantageously in a synergistic amount, advantageously in a quantity of 0.001 to 30% of dry matter, based on the total weight of the composition. The peptidic extract of avocado, added in the composition according to the invention, advantageously comprises 2 to 10 wt. % of alpha-amine nitrogen, based on the weight of the dry matter of the peptidic extract. It can be obtained according to a process such as that described above.

According to an advantageous variation of the invention, the composition further comprises a peptidic extract of lupine, advantageously in a synergistic amount, advantageously in a quantity of 0.001 to 30% of dry matter, based on the total weight of the composition. The peptidic extract of lupine, added in the composition according to the invention, comprises at least 70%, advantageously at least 80 wt. % of peptides, based on the weight of the dry matter of the peptidic extract. It can be obtained according to a process such as that described above.

The following examples illustrate the present invention, without limiting it in any way.

Example 1

Preparation of a Hydrosoluble Extract of Sugars from Avocado 50 kg of fresh avocados of the Hass variety were cut into thin slices of 2 to 5 mm thickness, stone included, by means of a disc slicer. The drying equipment was a thermo-regulated hot air flow oven. The sliced avocados were distributed at a thickness of 4 to 5 cm on the tiered racks. The drying temperature was set to 80° C. and the drying time was 48 hours. Once dried, the fruits were cold pressed. This operation was carried out with a small Komet® laboratory press.

The 4 kg of delipidised fruits (oil cake) were then ground cold and then extracted under reflux in the presence of 25 liters of ethanol. The powder, exempt of lipids, was then recovered by filtration through a Büchner funnel and dried in the oven for 5 hours at 50° C.

The oil cake was then washed with demineralised water (10 liters) and then separated by centrifugation. The soluble fraction (liquid) was taken up for purification and concentrated according to the following method:

Demineralisation by ion-exchange resins: demineralisation of the heptuloses by passage over OH⁻ resins then over H⁺ resin.

Ultrafiltration to 10000 Da: the ultrafiltration was carried out with a system equipped with 4 membranes with a threshold cut-off of 10 kDa.

Concentration under vacuum: The purified extract is concentrated down to a dry matter level of 4% by means of an evaporator under vacuum.

Packaging: the concentration of the extract is adjusted to 5% dry matter and the preservative is added, then it is filtered under sterile conditions with a membrane with a threshold of 0.2 µm and packaged.

Table 3 gives the composition of the extract in C7 sugars from avocado, at 5% dry matter, prepared according to the process described above:

TABLE 3

| Aspect | Pale yellow solution |
|---|---|
| Analytical criteria | |
| Dry matter | 5% |
| pH (dilution ¼) | 7.0 |
| Absorbance at 420 nm (dilution ¼) | 0.013 |
| Absorbance at 550 nm (dilution ¼) | 0.003 |
| Composition (% dry matter) | |
| Saccharose | 3.0 |
| Glucose | 7.5 |
| D-mannoheptulose | 40.0 |
| Fructose | 10.6 |
| Perseitol | 28.8 |

Two other extracts were prepared following the same process, and the pH, the absorbance and the C7 sugar content are given in Table 4 below. The C7 sugar content corresponds to the sum of the perseitol and D-mannoheptulose, analysed by HPLC.

TABLE 4

| | Batch | |
|---|---|---|
| | 1 | 2 |
| Dry matter | 5% | 5% |
| pH (dilution ¼) | 5.9 | 5.4 |
| Absorbance  420 nm (dilution ¼)  550 nm | 0.054 0.004 | 0.076 0.032 |
| C7 sugars/dry matter | 80.5 | 83.4 |

Example 2

Preparation of a Peptidic Extract of Avocado 50 kg of fresh avocados of the Hass variety were cut into thin slices of 2 to 5 mm thickness, stone included, by means of a disc slicer. The drying equipment was a thermo-regulated hot air flow oven. The sliced avocados were distributed at a thickness of 4 to 5 cm on the tiered racks. The drying temperature was set to 80° C. and the drying time was 48 hours. Once dried, the fruits were cold pressed. This operation was carried out with a small Komet® laboratory press. The 4 kg of delipidised fruits (oil cake) were then ground cold and then extracted under reflux in the presence of 25 liters of ethanol. The powder, exempt of lipids, was then recovered by filtration through a Büchner funnel and dried in the oven for 5 hours at 50° C. The oil cake was then washed with demineralised water (10 liters) and then separated by centrifugation. The solid fraction was taken up in an aqueous solution, acidified by HCl to a pH of 5, then contacted with 2% of cellulases, based on the dry matter. The duration of the hydrolysis was fixed at 6 hours.

The mixture was then centrifuged in the presence of adjuvant (2.5 wt. %/v). The recovered deposit was then subjected to a second hydrolysis at pH 8.0 in the presence of 0.5% Alcalase® (a commercial enzyme from the class of the proteases) at a temperature of 55° C. for two hours. The hydrolysis was maintained at constant pH by the continuous addition of 2M sodium hydroxide. Finally, the protease was denatured by heating at 85° C. for 10 minutes.

The resulting mixture was centrifuged and the supernatant liquid was filtered through a membrane of 7.5 μm. It was then subjected to ultrafiltration through membranes with a cut-off of 10 kD.

The resulting crude peptidic extract had 20% dry matter and was decolourised in the presence of 1% active charcoal Norit®, then filtered again through a membrane of 7.5 μm. The decolourised extract was then microfiltered (0.2 μm), diluted to a concentration of 5% dry matter, a preservative was then added (0.4 wt. %/v of Phenonip®) and the product was finally packaged. The properties of the hydrosoluble peptidic extract of avocado (5% dry matter) obtained by this process, are given in Table 5 below:

TABLE 5

| Aspect | Slightly orangey solution |
|---|---|
| Analytical criteria | |
| Dry matter | 5% |
| pH (dilution ¼) | 4.5 |
| Absorbance at 420 nm (dilution ¼) | 0.152 |
| Absorbance at 550 nm (dilution ¼) | 0.035 |
| Composition (% dry matter) | |
| Alpha-amine nitrogen | 6.7 |
| Proteins | not detected |
| Phenonip ® preservative | 0.4% |

Other extracts were prepared following the same process and the analytical data are given in Table 6 below.

TABLE 6

| | | Batch | | | |
|---|---|---|---|---|---|
| | | 1 | 2 | 3 | 4 |
| α-amine nitrogen (o-phthalaldehyde or ninhydrin method) (weight percent in the dry matter) | | 4.0 | 6.7 | 8.6 | 6.3 |
| Proteins (weight percent in the dry matter) (N * 6.25)[1] | | 10.4 | 22.1 | 24.9 | 15.5 |
| pH (dilution ¼) | | 4.7 | 4.5 | 5.7 | 5.3 |
| Absorbance | 420 nm | 0.315 | 0.150 | 0.982 | 0.499 |
| pH (dilution ¼) | 550 nm | 0.062 | 0.033 | 0.264 | 0.075 |

[1]N×6.25 corresponds to the total nitrogen content (N) of a sample multiplied by a specific coefficient for the analysed protein. When the coefficient for the analysed protein is not precisely known, then the coefficient 6.25 is used by convention.

In the aminogram given in Table 7 below, the values are given in weight percent based on the total weight of the analysed amino acids.

The values for aspartic acid and glutamic acid also include the asparagine and glutamine contents, respectively.

TABLE 7

| Amino acid | Results (averages) |
|---|---|
| Alanine | 7.1 |
| Arginine | 5.2 |
| Aspartic acid | 11.5 |
| Cystine | 3.2 |
| Glutamic acid | 14.5 |
| Glycine | 5.9 |
| Histidine | 2.4 |
| Isoleucine | 5.3 |
| Leucine | 8.5 |
| Lysine | 3.4 |
| Methionine | 1.4 |
| Phenylalanine | 5.2 |
| Proline | 4.7 |
| Serine | 6.1 |
| Threonine | 5.1 |
| Tyrosine | 4.0 |
| Valine | 6.5 |
| TOTAL | 100 |

Tryptophan not measured

In examples 3 to 7, unless indicated otherwise, the percentages are expressed in weight, based on the total weight of the dry matter.

Example 3

Induction of Beta Defensin-2 by the Sugars of Avocado

I. Inoculation of the Cells (J0):

The keratinocytes of normal humans were inoculated in a 96 well plaque (about 20000 cells/well), in the presence of a specific medium enriched in calcium (final concentration 1.3 mM), as previously described in the publication "Human β-Defensin-2 production in Keratinocytes is regulated by Interleukin-1, Bacteria, and the State of Differentiation", Alice Y. Liu et al., The Society for Investigative Dermatology, vol. 118, No. 2, February 2002, pages 275 to 281.

II. Treatment of Cells (J1):

After an incubation of 24 hours at 37° C., 5% $CO_2$:

2 rinses with 200 μl/well of PBS (phosphate buffer in saline solution)

stimulation of the cells by 200 μl/well (in a $Ca^{++}$ supplemented medium):

by the hydrosoluble extract of sugars of avocado at concentrations of 0.5, 0.05 and 0.005 w/w of dry matter by IL-1β at a concentration of 100 ng/ml (positive control of induction of hBD-2)

III. End of Treatment (J2): ELISA

After 24 hours of incubation, the induction of the hBD-2 was evaluated by an ELISA method with a specific antibody (goat polyclonal to human BD2; Abcam; ab9871). The results obtained with the hydrosoluble extract of sugars of avocado, batch A, comprising 40% of D-mannoheptulose and 40% perseitol, based on the dry weight, are summarised in Table 8 below:

TABLE 8

|  | Control cells | Positive control (IL-1β) | Batch A (0.005%) | Batch A (0.05%) | Batch A (0.5%) |
| --- | --- | --- | --- | --- | --- |
| hBD-2/MTT (OD) | 0.144 | 0.273 | 0.185 | 0.223 | 0.177 |
| hBD-2/MTT (OD) | 0.121 | 0.322 | 0.154 | 0.271 | 0.249 |
| hBD-2/MTT (OD) | 0.1 | 0.223 | 0.156 | 0.237 | 0.225 |
| hBD-2MTT (OD) | 0.136 | 0.324 | 0.21 | 0.297 | 0.271 |
| average | 0.125 +/− 0.017 | 0.285* +/− 0.041 | 0.176 +/− 0.023 | 0.257* +/− 0.029 | 0.231* +/− 0.035 |
| % increase vs. control | — | 128 | 41 | 105 | 84 |

*Statistically significant with respect to the control cells (p < 0.05 Student Test)
MTT: Methyl Thiazolyl Tetrazolium It was observed that the quantity of hBD-2 produced is increased by the hydrosoluble extract of sugars of avocado, batch A, according to the invention.

The results obtained with batch B, comprising 10%% of D-mannoheptulose and 70%% perseitol, based on the dry weight, are summarised in Table 9 below:
OD=optical density

TABLE 9

|  | Control cells | Positive control (IL-1β) | Batch B (0.005%) | Batch B (0.05%) | Batch B (0.5%) |
| --- | --- | --- | --- | --- | --- |
| hBD-2/MTT (OD) | 0.144 | 0.273 | 0.162 | 0.331 | 0.569 |
| hBD-2/MTT (OD) | 0.121 | 0.322 | 0.163 | 0.344 | 0.536 |
| hBD-2/MTT (OD) | 0.100 | 0.223 | 0.196 | 0.343 | 0.536 |
| hBD-2/MTT (OD) | 0.136 | 0.324 | 0.192 | 0.353 | 0.556 |
| average | 0.125 +/− 0.017 | 0.285* +/− 0.041 | 0.178* +/− 0.016 | 0.343* +/− 0.008 | 0.549* +/− 0.014 |
| % increase vs. control | — | 128 | 42 | 174 | 338 |

*Statistically significant with respect to the control cells (p < 0.05 Student Test)

It was observed that the production of hBD-2 is increased in a dosage dependent manner by the hydrosoluble extract of sugars of avocado, batch B.

Example 4

Effect of the Avocado Sugars on the Expression of hBD-2 in the Epithelial Cells

1. Cells

The cells KB (ATCC CCL-17), line of epithelial cells from a human oral carcinoma, commonly used in studies of the buccal cavity, were inoculated in plaques of 96 wells and cultivated in RPMI 1640 (Roswell Park Memorial Institute Medium) with Glutamax™1 at 10% VFS (veal fœtal serum)+ antibiotics.

2. Treatment

After 24 hours of incubation, the culture medium was eliminated and the cellular carpet was rinsed twice with PBS.

The cells were then treated under the conditions defined above during 24 and 48 hours:

Control cells: medium only
TNFα (commercialised by Sigma) at 100 ng/ml
hydrosoluble extract of sugars of avocado (40% mannoheptulose/40% perseitol) at 0.005-0.05 and 0.5 w/w (of dry matter) (batch A)

3. End of Treatment

Analysis of the antimicrobial peptides by ELISA on cells

After 48 hours of incubation under the different treatment conditions, the β-defensins 2 and 3 and the LL-present in the cells KB were analysed by an ELISA method on cells.

In order to determine the total number of cells in each well, a test with MTT was run in parallel on the cells treated under the same conditions.

Utilisation of the results

For each condition of treatment, the $OD_{450}$ AMPs (antimicrobial peptides) was divided by the $OD_{570}$ MTT to calculate the quantity of AMPs produced per living cell.

The averages and the standard deviations were calculated for each condition and the induction of different AMPS was calculated as the percentage increase with respect to the control cells.

4. Results

Induction of HBD-2

The TNF-α used here as the positive control of the induction of the AMPs causes a significant increase in the production of hBD-2 of 239% at 48 hours by the KB cells. This test validates the model.

The hydrosoluble extract of sugars of avocado also induces a statistically significant increase in the production of hBD-2 in the KB cells (see results in Table 10).

TABLE 10

| 48 hours | OD hBD2/OD MTT | | | | | | | standard deviation | Induction of HBD-2 | |
|---|---|---|---|---|---|---|---|---|---|---|
| | well 1 | well 2 | well 3 | well 4 | well 5 | well 6 | average | | % increase | significance Student Test |
| Negative control | 0.000 | 0.000 | 0.000 | 0.019 | 0.047 | 0.000 | 0.011 | 0.017 | | |
| TNFα 100 ng/ml | 0.048 | 0.036 | 0.027 | 0.047 | 0.046 | 0.018 | 0.037 | 0.011 | 239 | P < 0.05 |
| Batch A 0.005% | 0.052 | 0.004 | 0.031 | 0.058 | 0.038 | 0.012 | 0.032 | 0.020 | 198 | |
| Batch A 0.05% | 0.052 | 0.058 | 0.071 | 0.071 | 0.026 | 0.022 | 0.050 | 0.019 | 358 | P < 0.05 |
| Batch A 0.5% | 0.174 | 0.200 | 0.147 | 0.176 | 0.142 | 0.135 | 0.162 | 0.023 | 1387 | P < 0.01 |

Induction of HBD-3

The TNF-α used here as the positive control of the induction of the AMPs causes a significant increase in the production of hBD-3 of 30% at 48 hours by the KB cells. This test validates the model. The hydrosoluble extract of sugars of avocado also induces a statistically significant increase in the production of hBD-3 in the KB cells (see results in Table 11).

TABLE 11

| 48 hours | OD hBD3/OD MTT | | | | | | | standard deviation | Induction of HBD-3 | |
|---|---|---|---|---|---|---|---|---|---|---|
| | well 1 | well 2 | well 3 | well 4 | well 5 | well 6 | average | | % increase | significance Student Test |
| Negative control | 0.342 | 0.423 | 0.275 | 0.271 | 0.293 | 0.283 | 0.315 | 0.054 | | |
| TNFα 100 ng/ml | 0.431 | 0.448 | 0.399 | 0.407 | 0.374 | 0.399 | 0.410 | 0.024 | 30 | P < 0.01 |
| Batch A 0.005% | 0.448 | 0.432 | 0.338 | 0.423 | 0.321 | 0.329 | 0.382 | 0.053 | 21 | P < 0.05 |
| Batch A 0.05% | 0.514 | 0.481 | 0.441 | 0.410 | 0.436 | 0.427 | 0.451 | 0.035 | 43 | P < 0.01 |
| Batch A 0.5% | 0.451 | 0.492 | 0.436 | 0.429 | 0.417 | 0.489 | 0.452 | 0.029 | 44 | P < 0.01 |

Induction of LL-37

The TNF-α used here as the positive control of the induction of the AMPS causes a significant increase in the production of LL-37 of 88% at 48 hours by the KB cells. This test validates the model. The hydrosoluble extract of sugars of avocado also induces a statistically significant increase in the production of LL-37 in the KB cells (see results in Table 12).

TABLE 12

| 48 hours | OD LL-37/OD MTT | | | | | | | standard deviation | Induction of LL-37 | |
|---|---|---|---|---|---|---|---|---|---|---|
| | well 1 | well 2 | well 3 | well 4 | well 5 | well 6 | average | | % increase | significance Student Test |
| Negative control | 0.033 | 0.047 | 0.031 | | 0.046 | 0.054 | 0.042 | 0.009 | | |
| TNFα 100 ng/ml | 0.080 | 0.072 | 0.077 | 0.091 | 0.082 | 0.076 | 0.080 | 0.006 | 88 | P < 0.01 |
| Batch A 0.005% | 0.087 | 0.078 | 0.088 | 0.129 | 0.090 | 0.077 | 0.091 | 0.018 | 116 | P < 0.01 |
| Batch A 0.05% | 0.098 | 0.094 | 0.097 | 0.103 | 0.091 | 0.063 | 0.091 | 0.013 | 115 | P < 0.01 |
| Batch A 0.5% | 0.148 | 0.116 | 0.119 | | 0.173 | 0.119 | 0.135 | 0.022 | 219 | P < 0.01 |

In conclusion, it has been shown that the avocado sugars (hydrosoluble extract of sugars of avocado) are capable of inducing the synthesis of antimicrobial peptides, and notably the hBD-2, -3 and LL-37 in the KB type of epithelial cells.

Example 5

Effect of Avocado Sugars on Pro-inflammatory Molecules

Method:

The keratinocytes of normal humans were inoculated in a 24 well plaque (about 50000 cells/well), in the presence of a specific medium enriched in calcium (final concentration 1.3 mM), as previously described in the publication "Human β-Defensin-2 production in Keratinocytes is regulated by Interleukin-1, Bacteria, and the State of Differentiation", Alice Y. Liu et al., The Society for Investigative Dermatology, vol. 118, No. 2, February 2002, pages 275 to 281.

The cells were treated for 24 hours in the presence of 0.05% w/w of avocado sugars (batch A, 40% mannoheptulose/40% perseitol). The pro-inflammatory cytokines IL-1β, IL-8 and TNF-α were analysed by an ELISA method (kits R&D System) in the supernatant liquid of the culture. The cell viability was measured by a neutral red test. The results are expressed with respect to the OD neutral red so as to convert the quantity of cytokines produced to the quantity of living cells. (Tables 13, 14, 15).

Results:

TABLE 13

IL1β (pg/ml)/OD neutral red

|  | well 1 | well 2 | well 3 | average | standard deviation |
|---|---|---|---|---|---|
| Control cells | 0.093 | 0.048 | 0.149 | 0.097 | 0.042 |
| Cells + batch A at 0.05% MS | 0.058 | 0.009 | 0.012 | 0.026 | 0.022 |

TABLE 14

IL8((pg/ml)/OD neutral red

|  | well 1 | well 2 | well 3 | average | standard deviation |
|---|---|---|---|---|---|
| Control cells | 506.624 | 402.282 | 907.228 | 605.378 | 217.649 |
| Cells + batch A at 0.05% MS | 434.221 | 411.400 | 495.191 | 446.937 | 35.369 |

TABLE 15

TNFα (pg/ml)/OD neutral red

|  | well 1 | well 2 | well 3 | average | standard deviation |
|---|---|---|---|---|---|
| Control cells | 0.006 | 0.005 | 0.584 | 0.198 | 0.272 |
| Cells + batch A at 0.05% MS | 1.515 | 0.511 | 0.916 | 0.980 | 0.413 |

Conclusion: The avocado sugars (hydrosoluble extract of sugars of avocado) do not induce the production of pro-inflammatory molecules usually co-expressed with the beta-defensins (IL-1, IL-8, TNF-α). Therefore, the avocado sugars are inductors of AMPS but without being pro-inflammatory.

Example 6

Modulation of the Synthesis of HBD-2 by the Different Sugars Present in the Extract of Avocado Sugars The same test as in example 3 was carried out with:
a mixture of fructose (5%), glucose (5%) and saccharose (3%);
D-mannoheptulose (40%);
perseitol (40%);
a mixture of fructose (5%), glucose (5%) saccharose (3%) and D-mannoheptulose (40%);
a mixture of fructose (5%), glucose (5%) saccharose (3%) and perseitol (40%);
a mixture of fructose (5%), glucose (5%) saccharose (3%) D-mannoheptulose (40%) and perseitol (40%); and
an extract of avocado sugars (batch A).

The extract of avocado sugars comprises 40 wt. % of D-mannoheptulose and 40 wt. % of perseitol, based on the total weight of the dry matter.

The results are given in Table 16 below:

TABLE 16

| Sugar(s) tested: proportions corresponding to 1% of a 5% solution of MS of batch A, i.e. 0.05% MS | Modulation of the synthesis of HBD-2 % increase with respect to control cells) |
|---|---|
| mixture of fructose, glucose and saccharose | 0 |
| D-mannoheptulose | 31 |
| Perseitol | 12 |
| mixture of fructose, glucose, saccharose and D-mannoheptulose | 51 |
| mixture of fructose, glucose, saccharose and perseitol | 37 |
| mixture of fructose, glucose, saccharose, perseitol and D-mannoheptulose | 51 |
| avocado sugar | 49 |

The minority sugars of the avocado (fructose, glucose and saccharose) do not have any effect on the synthesis of HBD-2. For the same quantity (40 wt. % with respect to the weight of the dry matter), the D-mannoheptulose is more active than the perseitol. When the D-mannoheptulose and/or the perseitol is mixed with the minority sugars of avocado (fructose, glucose and saccharose), a synergistic effect is observed.

The mixture, fructose, glucose, saccharose, perseitol and D-mannoheptulose (reconstituted mixture), and the hydrosoluble extract of sugars of avocado obtained in example 1, have an equivalent activity.

Example 7

Activity of D-Mannoheptulose and Perseitol of Commercial Origin

The same test as in example 3 was carried out with commercially available D-mannoheptulose and perseitol. The results are given in Table 17 below:

TABLE 17

|  | Control Cells | IL-1 beta positive control | D-manno-heptulose (0.0012%) | D-manno-heptulose (0.012%) | Perseitol (0.0012%) | Perseitol (0.012%) |
|---|---|---|---|---|---|---|
| Average | 0.040 | 0.104 | 0.089 | 0.089 | 0.063 | 0.090 |

Tested separately, D-mannoheptulose and perseitol are capable of inducing the production of hBD-2.

Example 8

Effect of the Avocado Sugars on the Expression of hBD-2 Modulated by IL-4, in the Context of an In Vitro Modelling of Atopic Dermatitis The keratinocytes of normal humans were inoculated as described in example 3.

After 24 hours of incubation at 37° C., 5% of $CO_2$, the culture medium was eliminated and the cellular carpet was rinsed twice with PBS. The cells were then treated for 24 hours under the conditions defined below:

Control cells: medium only

IL-1β at 100 ng/ml (positive control for induction of hBD-2)

IL-4 at 50 ng/ml

Hydrosoluble extract of sugars of avocado (batch A) at 0.5% w/w of dry matter

IL-1β at 100 ng/ml and IL-4 at 50 ng/ml

IL-4 at 50 ng/ml and hydrosoluble extract of sugars of avocado (batch A) at 0.05% w/w of dry matter IL-1β at 100 ng/ml and IL-4 at 50 ng/ml and hydrosoluble extract of sugars of avocado (batch A) at 0.05% w/w of dry matter At the end of the treatment, the induction of hBD-2 was evaluated by an ELISA method on cells; in parallel, in order to determine the total number of cells in each well, a test with MTT was run in parallel on the cells treated under the same conditions. Thus, for each condition, the $OD_{450}$ hBD-2 was divided by the $OD_{570}$ MTT to obtain the quantity of hBD-2 produced per living cell.

The results are presented in Table 18 below:

TABLE 18

|  | Control cells | IL-1β (positive control) | IL-4 | batch A | IL-1β + IL-4 | IL-4 + batch A | IL-1β + IL-4 batch A |
|---|---|---|---|---|---|---|---|
| hBD-2/MTT (OD) | 0.176 | 0.308 | 0.158 | 0.240 | 0.261 | 0.210 | 0.606 |
| hBD-2/MTT (OD) | 0.175 | 0.347 | 0.163 | 0.309 | 0.177 | 0.214 | 0.519 |
| hBD-2/MTT (OD) | 0.173 | 0.291 | 0.160 | 0.225 | 0.209 | 0.263 | 0.504 |
| Average | 0.175 +/− 0.001 | 0.315** +/− 0.024 | 0.160 +/− 0.002 | 0.258* +/− 0.037 | 0.216*** +/− 0.035 | 0.229 +/− 0.024 | 0.543*** +/− 0.045 |

*$p < 0.01$;
**$p < 0.05$ with respect to the control cells (Student T test)
***$p < 0.05$ with respect to the positive control cells (Student T test)
****$p < 0.01$ with respect to IL-1β + IL-4 (Student T test)

The positive control IL-1β induces a significant increase in the synthesis of hBD-2 with respect to the control cells (+80%).

In the same way, the hydrosoluble extract of sugars of the avocado, batch A, increases the synthesis of hBD-2 (+48%).

The IL-4 alone, has no influence on the quantity of hBD-2 expressed by the keratinocytes.

In the presence of IL-4, the synthesis of hBD-2 induced by IL-1β is significantly inhibited by 32%.

Under these conditions, the addition of batch A to IL-1β+IL-4 again increases the synthesis of hBD-2: significant increase of 152% with respect to IL-1β+IL-4.

Conclusion:

Atopic dermatitis is characterised by a deficiency in anti-microbial peptides (hBD-2, hBD-3, LL-37). This deficiency can be explained, notably by a deregulation of the balance TH1/TH2 and an overproduction of the cytokines TH2 (IL-4 and IL-13). In this model, we have shown that the hydrosoluble extract of the sugars of the avocado is capable of opposing the inhibition of hBD-2 induced by IL-4. The avocado sugars are therefore of interest for containing atopic dermatitis.

Example 9

Inventive Cosmetic Formulations

Anti-acne Cream Nr. 1

| Isononyl Isononanoate | 7.000 |
|---|---|
| Di-$C_{12-13}$ Alkyl Malate | 7.000 |
| Isocetyl Stearate | 5.000 |
| Butylene glycol | 3.000 |
| Oriza Sativa | 2.500 |
| Hydrosoluble extract of avocado sugars | 3.000 |
| Dicaprylyl Ether | 2.000 |
| Salicylate of Silanediol | 2.000 |
| Arachnidic alcohol | 1.650 |
| Tromethamine | 1.180 |
| Cetyl alcohol | 1.000 |
| Salicylic acid | 1.000 |
| Ascorbyl glucoside | 1.000 |
| Glycine | 1.000 |
| Tocopheryl acetate | 1.000 |
| Behenyl alcohol | 0.900 |
| Squalane | 0.790 |
| Sodium Citrate | 0.660 |
| Copolymer PPG-12/SMDI | 0.500 |
| Arachidyl glucoside | 0.450 |
| Perfume | 0.400 |

-continued

| Gum sclerotium | 0.160 |
|---|---|
| Cetearyl alcohol | 0.130 |

Foaming Wash Emulsion for Acne Skins Nr. 1

| | |
|---|---|
| Citric acid | 0.110 |
| Sepigel 305* | 0.100 |
| Preservative system | QS |
| Water | QSP 100 |

*product commercialised by Seppic

Foaming Wash Emulsion for Acne Skins Nr. 1

| | |
|---|---|
| Water | QSP 100 |
| Arlatone duo* | 20.00000 |
| Glucoside of Coco- | 12.00000 |
| Guar hydroxypropyl | 2.00000 |
| Soluble extract of avocado sugars | 1.00000 |
| Hydrogenated glyceryl PEG-200 palmate | 1.10000 |
| PEG-7 Glyceryl cocoate | 1.10000 |
| Salicylate of Silanediol | 1.00000 |
| Cocamide DEA | 1.00000 |
| Caprylyol Glycine | 0.50000 |
| Potassium sorbate | 0.50000 |
| Polyquaternium 10 | 0.40000 |
| Perfume | 0.40000 |
| Citric acid | 0.30000 |
| Zinc PCA | 0.20000 |

*product commercialised by Quimasso

Foaming Wash Emulsion for Acne Skins Nr. 2

| | |
|---|---|
| Water | QSP 100 |
| Arlatone duo* | 20.00000 |
| Coco-Glucoside | 12.00000 |
| Guar hydroxypropy | 12.00000 |
| Soluble extract of avocado sugars | 2.00000 |
| Hydrogenated glyceryl PEG-200 palmate | 1.10000 |
| PEG-7 Glyceryl cocoate | 1.10000 |
| Salicylate of Silanediol | 1.00000 |
| Cocamide DEA | 1.00000 |
| Caprylol of glycine | 0.50000 |
| Potassium sorbate | 0.50000 |
| Polyquaternium 10 | 0.40000 |
| Perfume | 0.40000 |
| Citric acid | 0.30000 |
| Zinc PCA | 0.20000 |

*product commercialised by Quimasso

Toothpaste

| | |
|---|---|
| Water | QSP 100 |
| Soluble extract of avocado sugars | 2.00 |
| Sodium monofluorophosphate | 0.75 |
| Sodium fluoride | 0.10 |
| Sorbitol at 70% | 35 |
| Highly abrasive synthetic silica | 13 |
| Weakly abrasive synthetic silica | 5 |
| Sodium carboxymethylcellulose | 1.6 |
| sodium lauryl sulphate | 1 |
| Menthol aroma | 0.85 |
| Titanium dioxide | 0.5 |
| Lye | 0.5 |
| Sodium cyclamate | 0.3 |
| Menthol | 0.15 |
| Sodium saccharide | 0.07 |

Mouth Wash

| | |
|---|---|
| ACTMP 193 ® (lupine peptides) | 2.00 |
| Cremophor RH40 ® | 0.30 |
| Glycerine | 15 |
| Sodium saccharide | 0.03 |
| Soluble extract of avocado sugars | 1.00 |
| Aroma EUCA MINT | 0.08 |
| POBM | 0.20 |
| Potassium sorbate | 0.50 |
| Water | QSP 100 |

The invention claimed is:

1. A method for the protection of:
   healthy, immature skin of babies and children;
   pathological, immature skin of babies and children; or
   healthy or pathological skin of adult or elderly individuals,
   comprising the topical administration, to a patient in need thereof, of an effective amount of a composition comprising a hydrosoluble extract of sugars from avocado,
   wherein said sugars comprise D-mannoheptulose and perseitol, and
   wherein said composition stimulates antimicrobial peptides of the family of the cathelicidins and/or of the beta-defensins.

2. The method according to claim 1, wherein the composition comprises 0.001 to 30 wt. % of D-mannoheptulose, based on the total weight of said composition, and 0.001 to 30 wt. % of perseitol, based on the total weight of said composition.

3. The method according to claim 1, wherein said hydrosoluble extract of sugar from avocado is obtained by a process comprising the following successive steps:
   obtaining an avocado oil cake, optionally from the avocado fruit, by drying the avocado then extracting the lipids; then
   cryogenic grinding and total delipidation of said oil cake, then decanting and centrifuging so as to recover the soluble fraction rich in C7 sugars with elimination of the cake;
   demineralization over an ionic resin of said soluble fraction obtained from the preceding step; then
   ultrafiltration at 10 000 daltons; and
   concentration under vacuum and packaging.

4. The method according to claim 1, wherein said hydrosoluble extract of sugars from avocado comprises in weight, based on the total weight of the dry matter in the extract:

| | |
|---|---|
| D-mannoheptulose | 5 to 80% |
| Perseitol | 5 to 80% |
| Saccharose | less than 10% |
| Glucose | less than 10% |
| Fructose | less than 10%. |

5. The method according to claim 1, wherein the composition further comprises a peptidic extract of avocado.

6. The method according to claim 5, wherein said peptidic extract avocado comprises 2 to 10 wt. % of alpha-amine nitrogen, based on the weight of the dry matter of the peptidic extract.

7. The method according to claim 1, wherein the skin is sensitive skin, irritated skin, allergic skin, dry skin, aged skin, skin rendered fragile by an environmental aggression, or skin exhibiting cutaneous redness.

* * * * *